United States Patent
Chang (10) Patent No.: US 7,998,317 B2
(45) Date of Patent: Aug. 16, 2011

(54) GLYCEROL (MEDICAL GRADE) PREPARATION METHOD USING A BY-PRODUCT OF A BIO-DIESEL PROCESS

(76) Inventor: Wei Ming Chang, Taoyuan (TW)

(*) Notice: Subject to any disclaimer, the term of this patent is extended or adjusted under 35 U.S.C. 154(b) by 214 days.

(21) Appl. No.: 12/204,846

(22) Filed: Sep. 5, 2008

(65) Prior Publication Data

US 2010/0063332 A1    Mar. 11, 2010

(51) Int. Cl.
*B01D 1/22*    (2006.01)
*B01D 3/10*    (2006.01)
*B01D 3/12*    (2006.01)
*C07C 31/22*   (2006.01)

(52) U.S. Cl. .......... 203/18; 159/6.2; 159/49; 159/901; 159/DIG. 16; 202/176; 202/177; 202/205; 202/236; 203/21; 203/89; 203/94; 203/98; 203/DIG. 8; 568/852; 568/869

(58) Field of Classification Search ............... 159/6.2, 159/13.2, 49, 901, DIG. 16; 203/18, 21, 203/89, 91, 94, 98, DIG. 8, DIG. 23; 568/852, 568/868, 869; 202/176, 177, 205, 236

See application file for complete search history.

(56) References Cited

U.S. PATENT DOCUMENTS

| | | | | |
|---|---|---|---|---|
| 2,215,189 A | * | 9/1940 | Peterson | 203/89 |
| 2,741,638 A | * | 4/1956 | Blair et al. | 568/869 |
| 4,655,879 A | * | 4/1987 | Brockmann et al. | 203/37 |
| 7,709,667 B2 | * | 5/2010 | Kase et al. | 554/174 |

* cited by examiner

*Primary Examiner* — Virginia Manoharan
(74) *Attorney, Agent, or Firm* — Chun-Ming Shih (57) ABSTRACT

A glycerol preparation method for preparation of medical grade glycerol from a by-product of a bio-diesel process includes a first stage phosphoric acid chemical reaction process and a posterior by-product centrifugal separation process to have the phosphoric acid chemical reaction by-product be separated into free fatty acid, potassium phosphoric acid, and a crude glycerol and methanol mixture. The crude glycerol and methanol mixture is further processed through a first step of thin film evaporation process where methanol is reclaimed, a second step of thin film evaporation process where the mixture is dehydrated, a third step of molecular distillation process where an industrial grade glycerol of purity over 95% is extracted, and a fourth step of molecular distillation process where a medical grade glycerol of purity in exceed of 99.75% that meets USP/BP standards is extracted.

9 Claims, 8 Drawing Sheets

GLYCEROL (MEDICAL GRADE) PREPARATION METHOD USING A BY-PRODUCT OF A BIO-DIESEL PROCESS

BACKGROUND OF THE INVENTION

1. Field of the Invention

The present invention relates to a glycerol (medical grade) preparation method and more particularly, to a glycerol preparation method using a by-product of a bio-diesel process.

2. Description of the Related Art

It is known that making bio-diesel by transesterification of vegetable oil produces vegetable gel, crude glycerol, free fatty acid, methanol (or ethanol), and a saponified by-products consisting of potassium hydroxide.

These saponified by-products have commercial value, however they are harmful to the environment if they are not refined. Regular medium and small-scale bio-diesel refinery plants usually sell these by-products to the market at a price ranging from 200 to 250 US dollars per metric tone (fourth season, 2007) just because they have no technique or equipment to process these by-products.

There are companies which would provide special techniques for refining crude glycerol into refined glycerol. However, this investment takes a big amount of capital, few people make this investment. When received these by-products, most downstream manufacturers use a part of the by-products to make soap and then put the wastes into fuel oil for use as fuel, or prepare the wastes for making feed. Some other downstream manufactures may add these by-products to heavy fuel oil for use as fuel oil. The end products according to these methods have low added value. That's too bad.

SUMMARY OF THE INVENTION

The present invention has been accomplished under the circumstances in view. It is the main object of the present invention to provide a glycerol (medical grade) preparation method using a by-product of a bio-diesel process, which is to let a by-product of a bio-diesel process be treated through an acid reaction process to form a crystallized potassium phosphoric acid mixture, and then to separate the crystallized potassium phosphoric acid mixture into free fatty acid, crushed crystalloid potassium phosphoric acid and a crude glycerol and methanol mixture, and to treat the crude glycerol and methanol mixture through a continuous four-step thin film evaporation and molecular distillation procedure for enabling methanol to be reclaimed for use by the bio-diesel oil plant and crude glycerol to be further refined into an industrial grade or medical grade glycerol.

To achieve this and other objects of the present invention, the invention provides an efficient and automatic glycerol manufacturing process, which comprises:

1. Phosphoric Reaction Process

During this process, a transesterification by-product obtained from a bio-diesel process is stored in an accommodation tank, and then add 85% phosphoric acid at the ratio over 30% to the transesterification by-product and at the same time add a small amount of water to the transesterification by-product to have the transesterification by-product be blended into a mixture and then homogenized with phosphoric acid in a homogenizer so that potassium in the by-product is crystallized with phosphoric acid into crystallized potassium phosphoric acid with the rest in the form of a crude glycerol and methanol mixture. The by-product is separated through a three-phase stack disc separator into free fatty acid for use as a fuel, crushed crystalloid potassium phosphoric acid for making potassium phosphoric acid fertilizer, and a mixture of crude glycerol and methanol for further refining.

2. Methanol (or Ethanol) Reclaiming and Dehydration Process

The crude glycerol and methanol mixture is processed through a primary thin film evaporation process to extract methanol (or ethanol), and then a secondary thin film evaporation process to remove water from crude glycerol 3. Glycerol Refining Process Crude glycerol thus obtained is processed through a primary molecular distillation process so as to obtain an industrial glycerol of purity over 95%, and the industrial glycerol is then processed through a secondary molecular distillation process so as to obtain a medical grade glycerol of purity over 99.75%.

DETAILED DESCRIPTION OF THE PREFERRED EMBODIMENT

Figure 1:
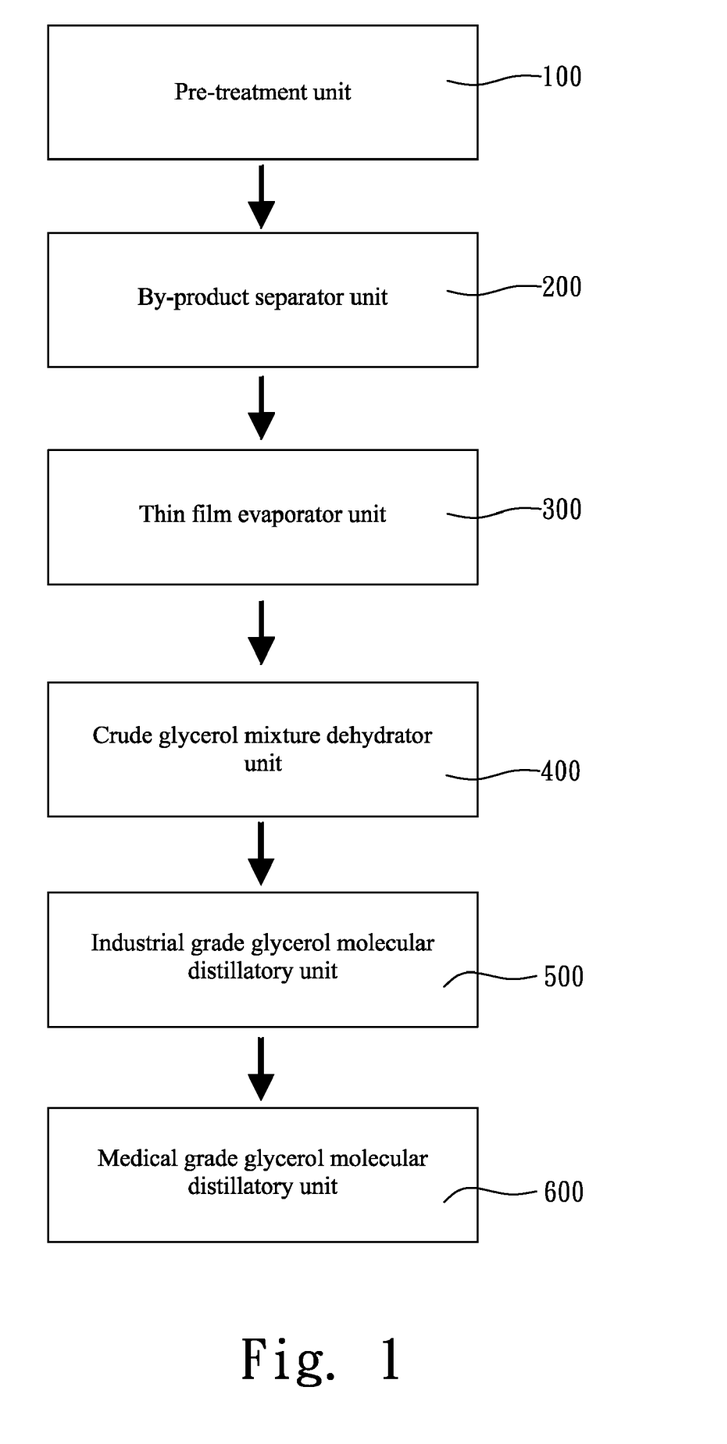
FIG. 1 is a glycerol preparation flow chart according to the present invention.

FIG. 1 is a glycerol preparation flow chart according to the present invention. A glycerol preparation method using a by-product of a bio-diesel fuel process requires a pre-treatment unit 100 for converting a transesterification by-product into a recyclable by-product, a by-product separator unit 200 for by-product separation, a thin film evaporator unit 300 for methanol recycling, a crude glycerol mixture dehydrator unit 400, and an industrial grade glycerol molecular distillatory unit 500, and a medical grade glycerol molecular distillatory unit 600. The aforesaid by-product is waste crude glycerol or saponified glycerol of a commercial bio-diesel fuel process.

Figure 2:
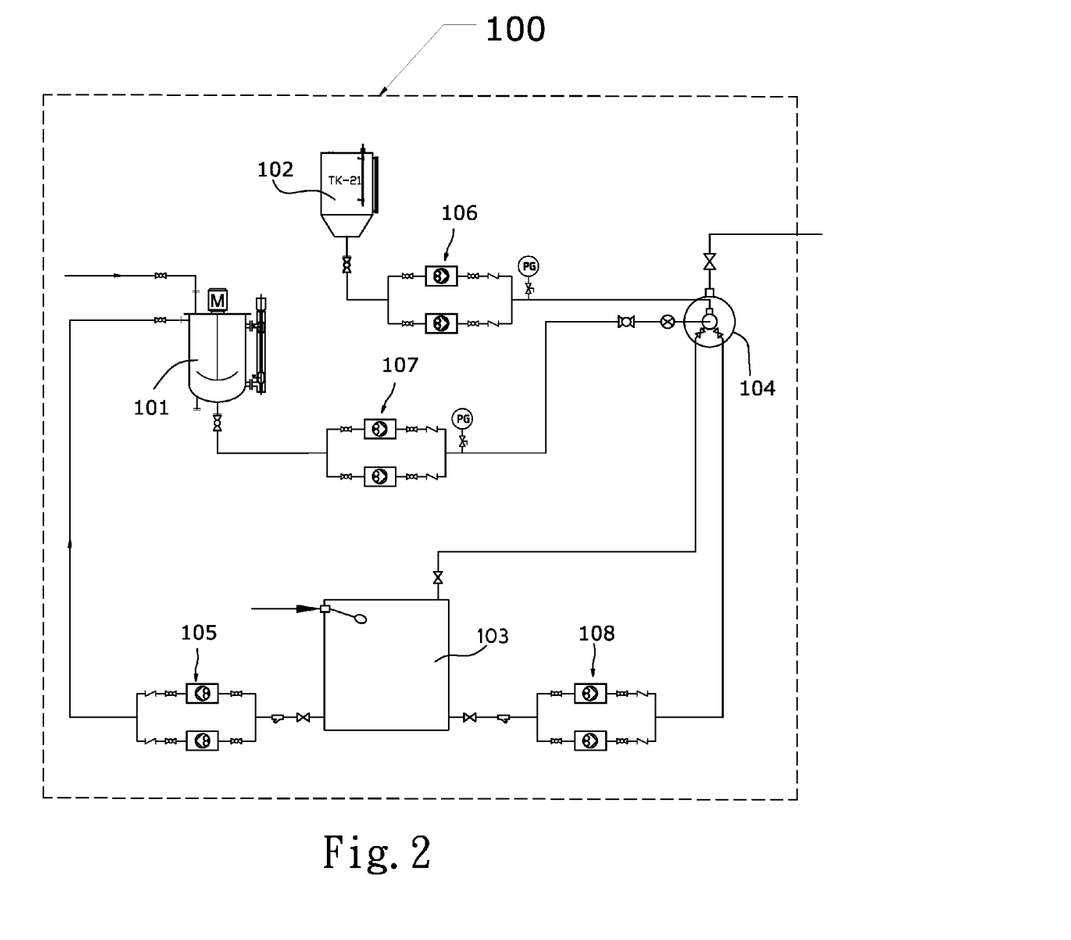
FIG. 2 is a schematic drawing showing the arrangement of the pre-treatment unit according to the present invention.

FIG. 2 illustrates an operation of the pre-treatment unit 100 in converting a transesterification by-product into a recyclable by-product. As illustrated, the pre-treatment unit 100 comprises a blending tank 101, a phosphoric acid tank 102, a clean water tank 103, a homogenizer 104, and delivery pumps 105~108.

During operation, put phosphoric acid purity 85% min. in the phosphoric acid tank 102 and guide clean water to the clean water tank 103, and then deliver the transesterification by-product to the blending tank 101, and then guide clean water from the clean water tank 103 to the blending tank 101 at a pre setting ratio and simultaneously guide phosphoric acid 85% from the phosphoric acid tank 102 to the homogenizer 104 at the ratio that the amount of phosphoric acid 85% is about 0.75~1% by weight of the amount of the transesterification by-product, thereby lowering the viscosity of the transesterification by-product. After blended, operate the delivery pump 107 to deliver the blended by-product from the blending tank 101 to the homogenizer 104 for homogenization. After homogenization, the homogenized by-product mixture is delivered to a feedstock tank 201 of the by-product separator unit 200 (see FIG. 3) for further separation process.

Figure 3:
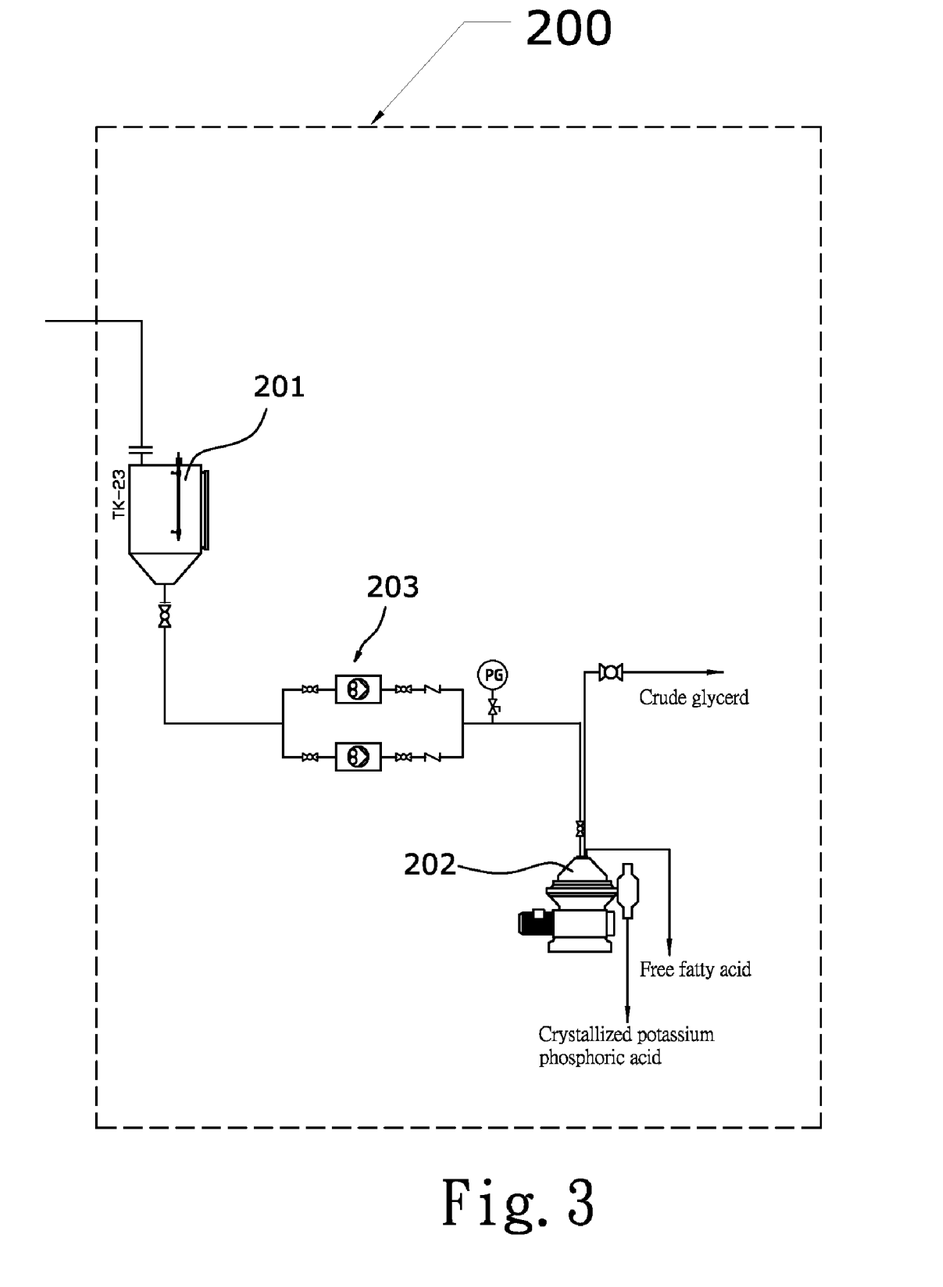
FIG. 3 is a schematic drawing showing the arrangement of the by-product separator unit according to the present invention.

As shown in FIG. 3, the by-product separator unit 200 comprises the aforesaid feedstock tank 201, a three-phase stack disc separator 202, and two delivery pumps 203. The homogenized by-product mixture obtained through the pretreatment unit 100 and stored in the feedstock tank 201 is further separated into free fatty acid, crushed crystalloid potassium phosphoric acid, and a mixture of crude glycerol, water and methanol (hereinafter referred to as crude glycerol mixture). Because these three substances have different mass and specific gravity, they can be separated by means of a three-phase high-speed stack disc separator.

During actual operation, start the delivery pump 203 to deliver the homogenized by-product mixture from the feedstock tank 201 to the three-phase stack disc separator 202, for enabling free fatty acid, crystallized potassium phosphoric acid and crude glycerol to be separated from the homogenized by-product mixture. Separated free fatty acid can be used as an animal feed additive, or added to a heavy oil as a fuel, crystallized potassium phosphoric acid can be sold to a fertilizer plant for making potassium phosphate fertilizer, and crude glycerol mixture is pumped to a storage of a next processing state as feedstock for further glycerol refining.

Figure 4:
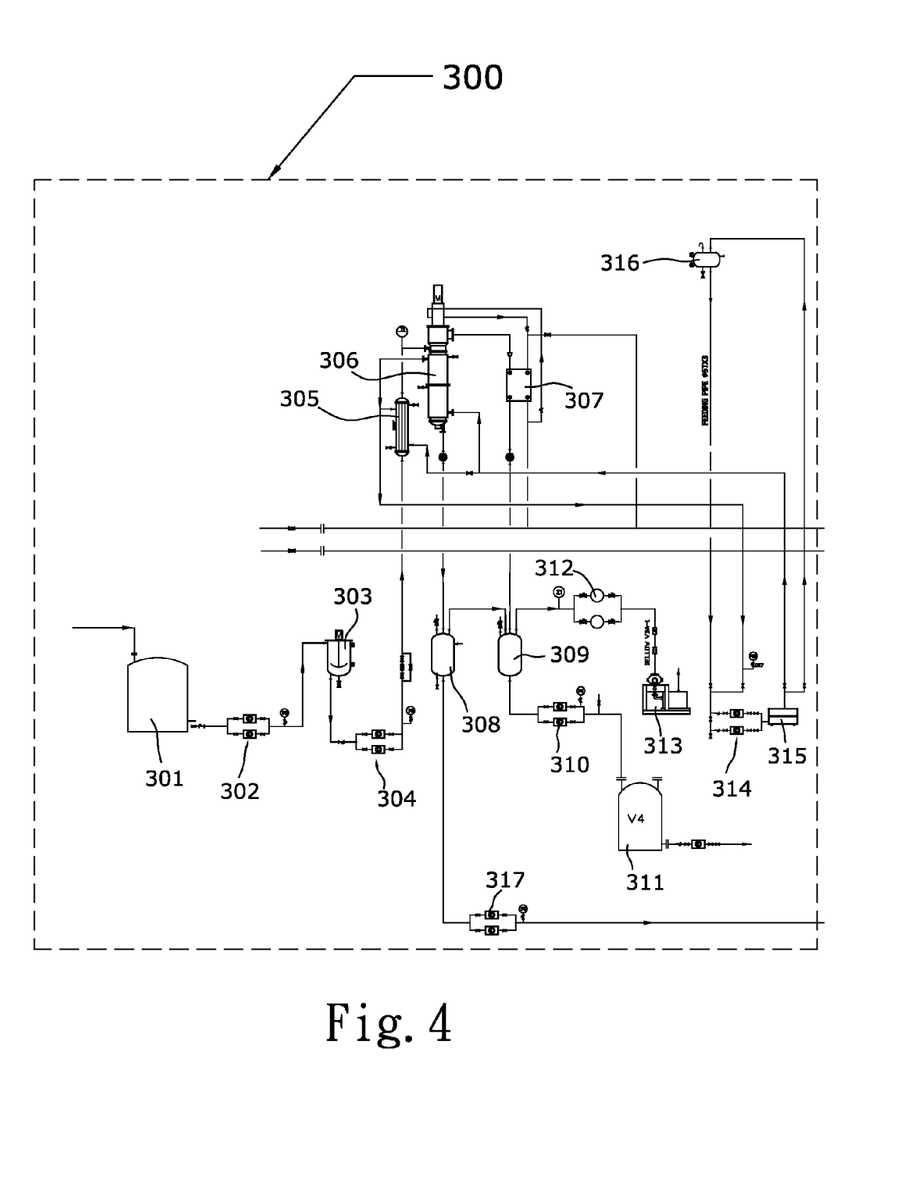
FIG. 4 is a schematic drawing showing the arrangement of the thin film evaporator unit according to the present invention.

FIG. 4 is a schematic drawing showing the arrangement of the thin film evaporator unit according to the present invention. Crude glycerol mixture obtained from the aforesaid transesterification through the aforesaid by-product the pretreatment unit 100 (see FIG. 2) and by-product separator unit 200 (see FIG. 3) contains methanol, water, crude glycerol (about 50~85%) and MONG (matter of non organic). Because these substances have different distilled points, two thin film evaporators and two molecular evaporators are necessary for separating these substances under different working temperatures so as to obtain refined glycerol. The procedure is outlined hereafter:

At first, the thin film evaporator unit 300 for methanol recycling requires a feedstock blending tank 301, a first delivery pump 302, a feedstock adjustment tank 303, a second delivery pump 304, a pre-heater 305, a wiper type thin film evaporator 306, a heat exchanger 307, a semi-finished product accommodation tank 308, a methanol accommodation tank 309, a third delivery pump 310, methanol storage tank 311, at least one gas-liquid separator 312, a vacuum pump 313, a thermal oil circulation pump 314, a thermal oil heater 315, an expansion tank 316, a fourth delivery pump 317, and related piping, thermostat means, fluid level control means, control valve means, operating wheel means and the like for system composition and component parts connection. Further, the thin film evaporator unit 300 is used with a functional public facility 700 that comprises a cooling tower 701 and water pumps 702A/B/C/D and a water chiller 703 (see FIG. 8).

Further, during operation, cooling water is guided into the thin film evaporator unit 300 to cool down the mechanical seal means of the wiper type thin film evaporator 306 and vacuum pump 313 and condensing coil means of the heat exchanger 307.

During operation, the cooling tower 701 and the water pumps 702A/B/C/D are started, and then the thermal oil circulation pump 314 is started to pump a thermal oil from the thermal oil heater 315 through the expansion tank 316 to the pre-heater 305 and the wiper type thin film evaporator 306 and then to the thermal oil heater 315 again, finishing one circulation cycle. Thereafter, set the thermal oil working temperature, and then start the thermal oil heater 315 to heat the thermal oil to about 140° C.

Thereafter, start the vacuum pump 313 to draw air from the related pipeline, the wiper type thin film evaporator 306, the semi-finished product accommodation tank 308 and the methanol accommodation tank 309, lowering the pressure of the whole feeding and catching pipeline system to below 100 mBar (0.1 bar). During this vacuum extraction process, gas is separated by the gas-liquid separator 312 and driven into the atmosphere by the vacuum pump 313 through an exhaust port.

Thereafter, start the first delivery pump 302 to pump feedstock (crude glycerol mixture) from the feedstock blending tank 301 to the feedstock adjustment tank 303 for conditioning, and then start the second delivery pump 304 to pump the conditioned crude glycerol mixture from the feedstock adjustment tank 303 to the pre-heater 305 where the crude glycerol mixture is heated to above 58° C., and then to the inside of the cylinder of the wiper type thin film evaporator 306 where the wiper of the wiper type thin film evaporator is continuously rotated to apply the crude glycerol mixture to an inner cylindrical wall of the cylinder of the wiper type thin film evaporator evenly, forming a feedstock thin film of thickness about 4~5/1000 mm (4μ~5μ). Because 140° C. thermal oil is delivered through the space between the inner cylindrical wall and outer casing of the cylinder of the wiper type thin film evaporator 306, the temperature of the feedstock thin film is then capable of being maintained. Further, because the working pressure inside the feeding and catching pipeline is kept under the negative pressure of 100 mBar, methanol molecules are evaporated from the feedstock thin film under this negative pressure environment before reaching 63° C. distillation temperature. Methanol steam goes through the pipeline into the heat exchanger 307 where methanol steam is condensed into fluid and guided into the methanol accommodation tank 309. When the liquid methanol in the methanol accommodation tank 309 reaches a pre setting high level, the third delivery pump 310 is started to pump liquid methanol out of the methanol accommodation tank 309 to the methanol storage tank 311.

The by-product that is not recycled, i.e., crude glycerol mixture is not distillable at 58° C. and therefore it falls along the inner cylindrical wall of the cylinder of the wiper type thin film evaporator 306 into the semi-finished product accommodation tank 308. When the level of crude glycerol mixture in the semi-finished product accommodation tank 308 surpasses a pre setting range, the fourth delivery pump 317 is started to pump crude glycerol mixture out of the semi-finished product accommodation tank 308 to the next unit for dehydration.

When at 1 ATM, the distillation temperature of methanol is 63° C. However, methanol is evaporated at 58° C. when under the working pressure 100 mBar. This design avoids exposure of glycerol composition to a high temperature environment to affect its quality, and eliminates the risk of approaching of methanol steam to flash point.

Figure 5:
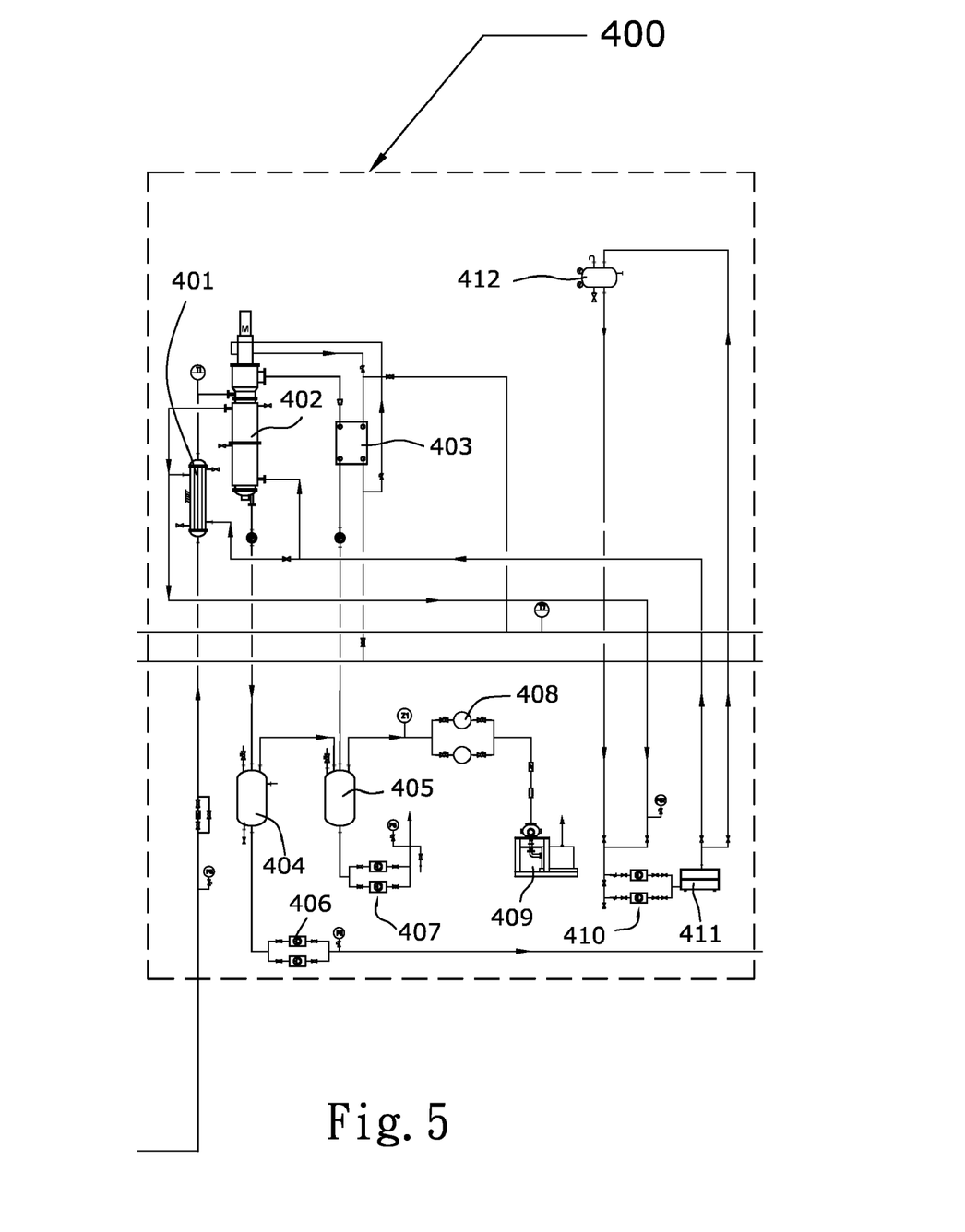
FIG. 5 is a schematic drawing showing the arrangement of the crude glycerol mixture dehydrator unit according to the present invention.

FIG. 5 is a schematic drawing showing the arrangement of the crude glycerol mixture dehydrator unit according to the present invention. As illustrated, the crude glycerol mixture dehydrator unit 400 comprises a pre-heater 401, a wiper type thin film evaporator 402, a heat exchanger 403, a semi-finished product accommodation tank 404, a waste water reclaim tank 405, a semi-finished product output pump 406, a waste water reclaim tank 407, an on-line gas-liquid separator 408, a vacuum pump 409, a thermal oil circulation pump 410, a thermal oil heater 411, a thermal oil expansion tank 412, and related piping, thermostat means, fluid level control means, control valve means, operating wheel means and the like for system composition and component parts connection. Further, the crude glycerol mixture dehydrator unit 400 is used with the cooling tower 701 and water pumps 702A/B/C/D of the aforesaid functional public facility 700 (see FIG. 8).

Before operation, cooling water is guided into the crude glycerol mixture dehydrator unit 400 to cool down the mechanical seal means of the wiper type thin film evaporator 402 and vacuum pump 409 and condensing coil means of the heat exchanger 403.

During operation, start the thermal oil circulation pump 410 to pump a thermal oil from the thermal oil heater 411 through the expansion tank 412 to the pre-heater 401 and the wiper type thin film evaporator 402 and then to the thermal oil heater 411 again, finishing one circulation cycle. Thereafter, set the thermal oil working temperature at 170° C., and then start the thermal oil heater 411 to heat the thermal oil to about 170° C.

Thereafter, start the vacuum pump 409 to draw air from the related pipeline, the wiper type thin film evaporator 402, the semi-finished product accommodation tank 404 and the waste water reclaim tank 405, lowering the pressure of the whole feeding and catching pipeline system to below 100 mBar. During this vacuum extraction process, gas is separated by the gas-liquid separator 408 and driven into the atmosphere by the vacuum pump 409 through an exhaust port.

When the level of crude glycerol mixture in the semi-finished product accommodation tank 308 of the last thin film evaporator unit 300 surpasses a pre setting range, the fourth delivery pump 317 of the thin film evaporator unit 300 is started to pump crude glycerol mixture out of the semi-finished product accommodation tank 308 through the pre-heater 401, where the crude glycerol mixture is heated to above 95° C., and then to the inside of the cylinder of the wiper type thin film evaporator 402 where the wiper of the wiper type thin film evaporator is continuously rotated to apply the crude glycerol mixture to the inner cylindrical wall of the cylinder of the wiper type thin film evaporator evenly, forming a feedstock thin film of thickness about 4~5/1000 mm (4μ~5μ). Because 170° C. thermal oil is delivered through the space between the inner cylindrical wall and outer casing of the cylinder of the wiper type thin film evaporator 402, the temperature of the feedstock film is then capable of being maintained. Further, because the working pressure inside the feeding and catching pipeline is kept under the negative pressure of 100 mBar, water is evaporated from the feedstock film at 95° C. under this negative pressure environment. At this time, steam goes through the output pipeline into the heat exchanger 403 where steam is condensed into water that is guided into the waste water reclaim tank 405.

The by-product that is not recycled, i.e., crude glycerol mixture is not distillable at 95° C. and therefore it falls along the inner cylindrical wall of the cylinder of the wiper type thin film evaporator 402 into the semi-finished product accommodation tank 404. When the level of crude glycerol mixture in the semi-finished product accommodation tank 404 surpasses a pre setting range, the semi-finished product output pump 406 is started to pump crude glycerol mixture out of the semi-finished product accommodation tank 404 to the next unit for further refining.

The distillation temperature of water is 100° C. However, water is evaporated at 95° C. when under the working pressure 100 mBar. This design avoids exposure of glycerol composition to a high temperature environment and emulsification of glycerol by steam, thereby maintaining the product quality.

Figure 6:
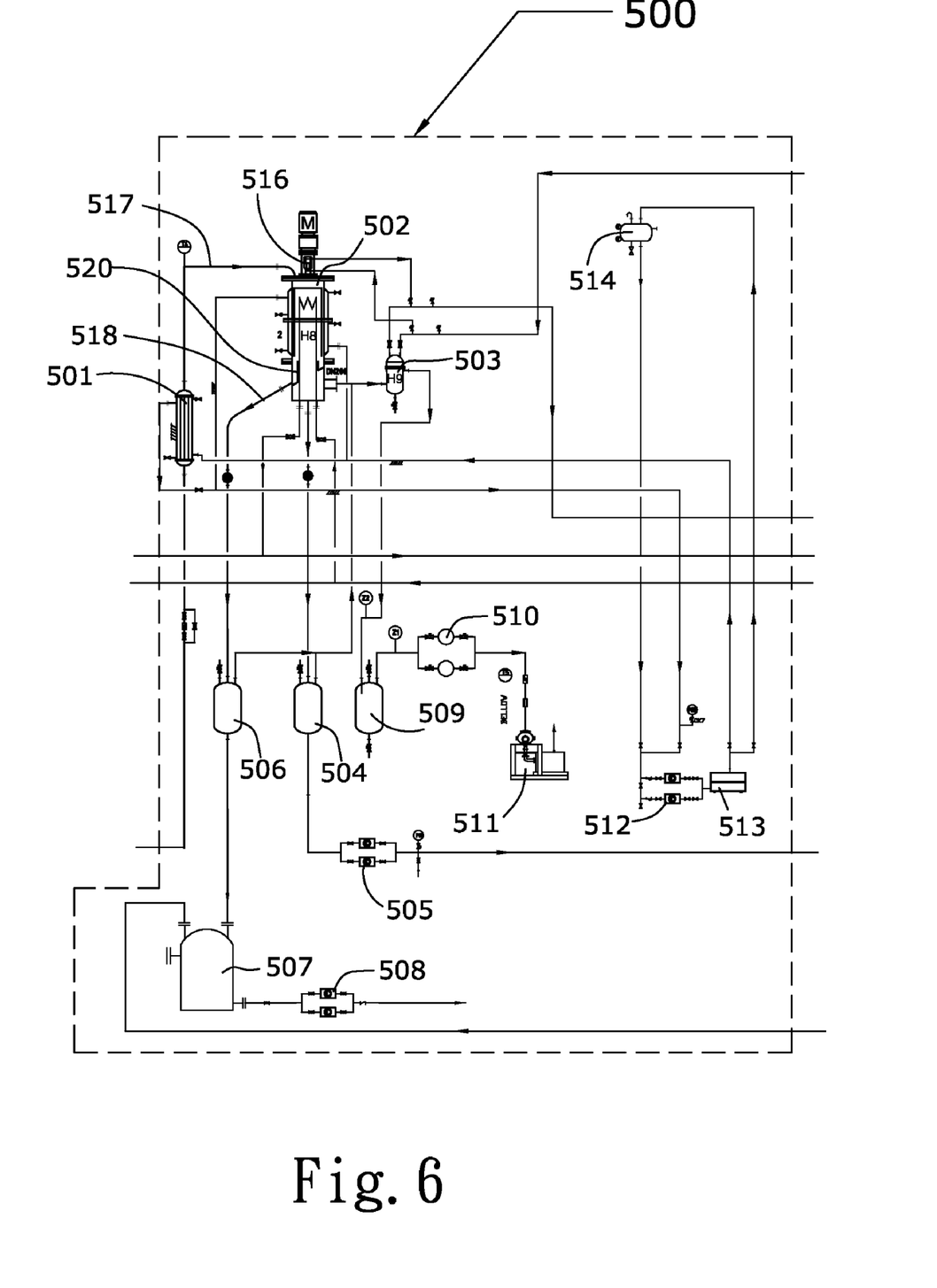
FIG. 6 is a schematic drawing showing the arrangement of the industrial grade glycerol molecular distillatory unit according to the present invention.

FIG. 6 is a schematic drawing showing the arrangement of the industrial grade glycerol molecular distillatory unit according to the present invention. As illustrated, the industrial grade glycerol molecular distillatory unit 500 is adapted for refining industrial grade glycerol of purity over 95%, comprising a pre-heater 501, a wiper type molecular still 502, a cold well 503, a semi-finished product accommodation tank 504, a semi-finished product output pump 505, a by-product accommodation tank 506, a by-product buffer tank 507, a by-product output pump 508, a vacuum buffer tank 509, an on-line gas-liquid separator 510, a vacuum pump 511, a thermal oil circulation pump 512, a thermal oil heater 513, a thermal oil expansion tank 514 and related piping, thermostat means, fluid level control means, control valve means, operating wheel means and the like for system composition and component parts connection. Further, the industrial grade glycerol molecular distillatory unit 500 is used with the cooling tower 701 and water pumps 702A/B/C/D of the aforesaid functional public facility 700 (see FIG. 8).

Before operation, cooling water is guided into the industrial grade glycerol molecular distillatory unit 500 to cool down the condensing coil means of the wiper type molecular still evaporator 502 and the mechanical seal means of the vacuum pump 511.

Figure 8:
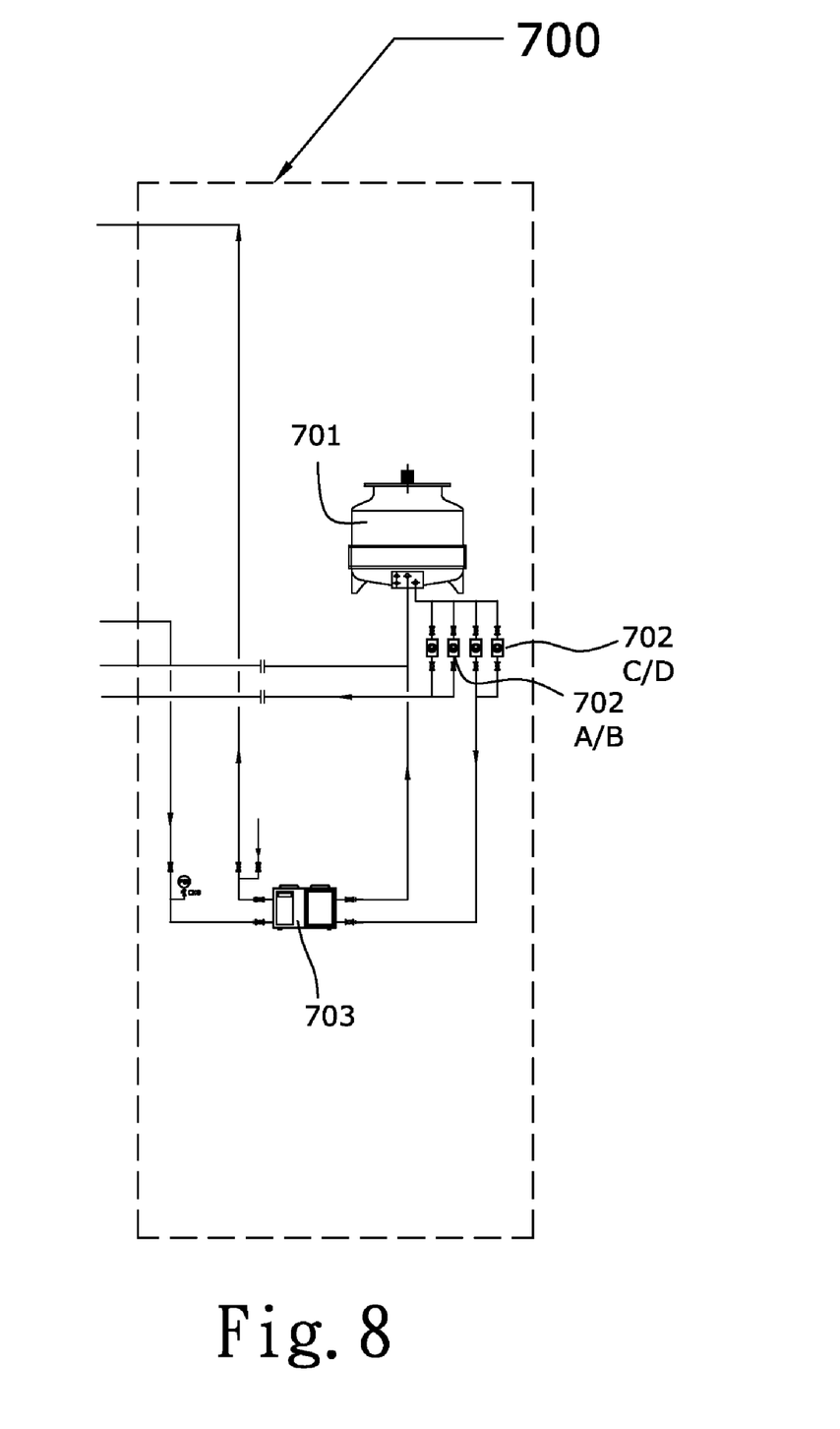
FIG. 8 is a schematic drawing of a public facility constructed according to the present invention.

During operation, add clean water and ethylene glycol to the water chiller 703 of the functional public facility 700 at the ratio that the amount of ethylene glycol is about 65% of the total water amount, and then start the water chiller 703 to make chilled water, enabling produced chilled water to be pumped by the internal chilled water pump of the water chiller 703 to the condensing loop of the cold well 503 and the mechanical seal means cooling loop 516 of the wiper type molecular still 502 and then to the chilled water tank of the water chiller 703, forming a circulation loop. This chilled water circulation process is repeated again and again till that the temperature of the chilled water in the pipeline reaches −10° C.

Thereafter, start the thermal oil circulation pump 512 to pump a thermal oil out of the thermal oil heater 513 through the expansion tank 514, the pre-heater 501 and a sandwich structure of the wiper type molecular still 502 and then the thermal oil heater 513 again, finishing one circulation cycle. Thereafter, set the thermal oil working temperature at 240° C., and then start the thermal oil heater 513 to heat the thermal oil to 240° C.

Thereafter, start the vacuum pump 511 to draw air from the related pipeline system of the industrial grade glycerol molecular distillatory unit 500, the wiper type molecular still 502 and the semi-finished product accommodation tank 504, lowering the pressure of the whole feeding and catching pipelines 517, 518 to below 40 Pa. During this vacuum extraction process, gas is separated by the gas-liquid separator 510 and driven into the atmosphere by the vacuum pump 511 through an exhaust port.

When the level of crude glycerol mixture in the semi-finished product accommodation tank 404 of the crude glycerol mixture dehydrator unit 400 surpasses a pre setting range, the semi-finished product output pump 406 is started to pump crude glycerol mixture out of the pre-heater 501, where the crude glycerol mixture is heated to above 195° C., and then to the inside of the cylinder of the wiper type molecular still 502 where the wiper of the wiper type molecular still is continuously rotated to apply the crude glycerol mixture to the inner cylindrical wall of the cylinder of the wiper type molecular still evaporator evenly, forming a feedstock thin film of thickness about 4~5/1000 mm (4μ~5μ). Because 240° C. thermal oil is delivered through the space between the inner cylindrical wall and outer casing of the cylinder of the wiper type molecular still 502, heat is rapidly transferred to the oil membrane of the feedstock to keep its temperature at a range above 195° C. Further, because the working pressure inside the feeding and catching pipelines 517, 518 is kept under the negative pressure of 40 Pa, glycerol is evaporated from the oil membrane of the feedstock at 195° C. under this negative pressure environment. At this time, glycerol molecules start to fly. When touched the internal condenser of the wiper type molecular still evaporator 502, glycerol steam is condensed into fluid, which flows along the pipeline into the semi-finished product accommodation tank 504. When the level of the fluid in the semi-finished product accommodation tank 504 reaches a pre setting high level, the semi-finished product output pump 505 automatically pumps the semi-finished product out of the semi-finished product accommodation tank 504 to the next unit for further glycerol refining.

The by-product that is not recycled is a fluid mixture of flock-like solid matter, animal gel and inorganic substance. Because of heavy molecular weight, the molecular free path of this mixture cannot reach the internal condenser of the wiper type molecular still 502. Therefore, this fluid mixture falls to the bottom side of the wiper type molecular still 502 and collected by a collector board 520 and then guided to the by-product buffer tank 507. When the level of the fluid mixture in the by-product buffer tank 507 reaches a pre setting high level, the by-product output pump 508 is immediately started to pump the fluid mixture out of the by-product buffer tank 507 to an external storage tank for sale. On the other hand, the semi-finished glycerol that falls to the semi-finished product accommodation tank 504 has a purity over 95%, and therefore it can be sold as industrial grade glycerol, or used as feedstock for refining into medial grade glycerol. According to the present preferred embodiment, when the level of the fluid in the semi-finished product accommodation tank 504 reaches a pre setting high level, the semi-finished product output pump 505 automatically pumps the semi-finished product out of the semi-finished product accommodation tank 504 to the next unit for further refining into medical grade glycerol.

Further, a part of the glycerol composition of the material that is delivered to the first glycerol refinery process that has a light molecular mass cannot be condensed by the internal condenser of the wiper type molecular still 502 during molecular distillation, and will escape out of the wiper type molecular still 502 and fly to the inside of the shade of the cold well 503. Because the temperature of the fog-like glycerin molecules is as high as 195° C., very low temperature chilled water therefore is used to make a heat exchange with the internal condenser of the cold well 503, enabling these light mass glycerol molecules to be condensed and guided into the vacuum buffer tank 509. Therefore, the water chiller 703 must pump chilled water into the condenser pipeline of the cold well 503 continuously for heat exchange with the residual glycerol molecules that are not condensed in the wiper type molecular still 502 and that escape out of the wiper type molecular still 502.

Under atmospheric pressure, the distillation temperature of glycerol is about 250~290° C. However, because the working pressure in the wiper type molecular still 502 is below 40 Pa, glycerol start to evaporate at 195° C. This design avoids exposure of glycerol composition to a high temperature environment to affect its quality.

Figure 7:
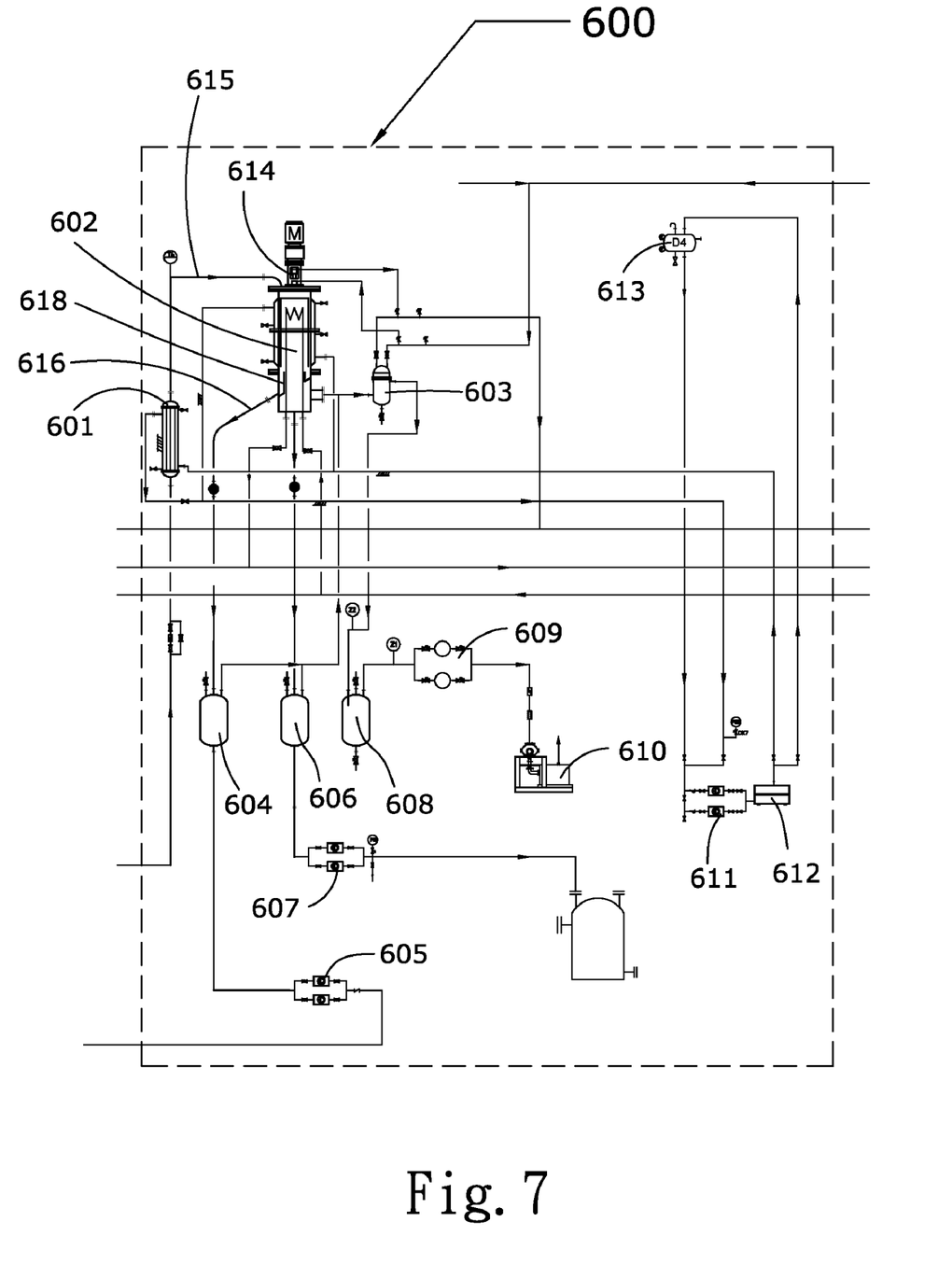
FIG. 7 is a schematic drawing showing the arrangement of the medical grade glycerol molecular distillatory unit according to the present invention.

FIG. 7 is a schematic drawing showing the arrangement of the medical grade glycerol molecular distillatory unit for refining medical grade glycerol according to the present invention. The medical grade glycerol molecular distillatory unit 600 is adapted for processing the industrial grade glycerol thus obtained from the aforesaid the industrial grade glycerol molecular distillatory unit 500 into a medical grade glycerol having a purity over 99.75%.

This equipment of the medical grade glycerol molecular distillatory unit 600 is same as the aforesaid the industrial grade glycerol molecular distillatory unit 500. The feedstock for this refining process is a high purity industrial glycerol, and the product of this refining process is a medical grade glycerol having a purity over 99.75%.

As illustrated, the medical grade glycerol molecular distillatory unit 600 comprises a pre-heater 601, a wiper type molecular still 602, a cold well 603, a by-product accommodation tank 604, a by-product output pump 605, a finished product accommodation tank 606, a finished product output pump 607, a vacuum buffer tank 608, an on-line gas-liquid separator 609, a vacuum pump 610, a thermal oil circulation pump 611, a thermal oil heater 612, a thermal oil expansion tank 613, and related piping, thermostat means, fluid level control means, control valve means, operating wheel means and the like for system composition and component parts connection. Further, the medical grade glycerol molecular distillatory unit 600 is used with the cooling tower 701 and water pumps 702A/B/C/D of the aforesaid functional public facility 700 (see FIG. 8).

During actual practice, make sure that the cooling tower 701 and water pumps 702A/B/C/D of the aforesaid functional public facility 700 have been started, and cooling water has guided into the mechanical seal means and condenser of the wiper type molecular still 602 and the mechanical seal means of the vacuum pump 610, and the cooling loop of the water chiller 703.

Make sure that the water chiller 703 has been started to make chilled water, the chilled water pump of the water chiller 703 has been started to pump chilled water to the condensing loop of the cold well 603 and the mechanical seal means cooling loop 616 of the wiper type molecular still 602 and then to the chilled water tank of the water chiller 703, forming a circulation loop.

Thereafter, start the thermal oil circulation pump 611 to pump a thermal oil from the thermal oil heater 612 through the expansion tank 613, the pre-heater 601 and a sandwich structure of the wiper type molecular still 602 and then the thermal oil heater 612 again, finishing one circulation cycle. Thereafter, set the thermal oil working temperature at 240° C., and then start the thermal oil heater 612 to heat the thermal oil to 240° C.

Thereafter, start the vacuum pump 610 to draw air from the related pipeline system of the medical grade glycerol molecular distillatory unit 600, the wiper type molecular still 602 and the finished product accommodation tank 606, lowering the pressure of the whole feeding and catching pipelines 617, 618 to below 40 Pa. During this vacuum extraction process, gas is separated by the gas-liquid separator 609 and driven into the atmosphere by the vacuum pump 610 through an exhaust port.

When the level of the fluid in the semi-finished product accommodation tank 504 reaches a pre setting high level, the semi-finished product output pump 505 automatically pumps the semi-finished product out of the semi-finished product accommodation tank 504 through the pre-heater 601 where the feedstock, industry glycerol from the previous process is heated to above 195° C., and then to the inside of the cylinder of the wiper type molecular still 602 where the wiper of the wiper type molecular still is continuously rotated to apply the crude glycerol mixture to the inner cylindrical wall of the cylinder of the wiper type molecular still evaporator evenly, forming a feedstock thin film of thickness about 4~5/1000 mm (4μ~5μ). Because 240° C. thermal oil is delivered through the space between the inner cylindrical wall and outer casing of the cylinder of the wiper type molecular still 602, heat is rapidly transferred to the oil membrane to keep the oil membrane temperature above on 195° C. Further, because the working pressure inside the feeding and catching pipelines 617, 618 is kept under the negative pressure of 40 Pa, glycerol is evaporated from the oil membrane of the feedstock at 195° C. under this negative pressure environment. At this time, glycerol molecules start to fly. When touched the internal condenser of the wiper type molecular still 602, glycerol steam is condensed into fluid, which flows along the pipeline into the finished product accommodation tank 606. When the level of the finished product in the finished product accommodation tank 606 reaches a pre setting high level, the finished product output pump 607 automatically pumps the finished product out of the finished product accommodation tank 606 to external storage means for further packaging for sale.

The by-product that is not recycled is a fluid mixture of flock-like solid matter, gel and/or inorganic substance. Because of heavy molecular weight, the molecular free path of this mixture cannot reach the internal condenser of the wiper type molecular still 602. Therefore, this fluid mixture falls to the bottom side of the wiper type molecular still 602 and collected by a collector board 620 and then guided to the by-product buffer tank 604. When the level of the fluid mixture in the by-product buffer tank 604 reaches a pre setting high level, the by-product output pump 605 is immediately started to pump the fluid mixture out of the by-product buffer tank 604 to an external storage tank for sale. On the other hand, the finished product that falls to the finished product accommodation tank 606 has a purity in exceed of 99.75%, reaching the requirement for medical application. Further, a part of the glycerol composition of the material under this glycerol refinery process that has a light molecular mass cannot be condensed by the internal condenser of the wiper type molecular still 602 during molecular distillation, and will escape out of the wiper type molecular still 602 and fly to the inside of the shade of the cold well 603. Because the temperature of the fog-like glycerin molecules is as high as 195° C., very low temperature chilled water therefore is used to make a heat exchange with the internal condenser of the cold well 603, enabling these light mass glycerol molecules to be condensed and guided into the vacuum buffer tank 608. Therefore, the water chiller 703 must pump chilled water into the condenser pipeline of the cold well 603 continuously for heat exchange with these fog-like glycerol molecules to have these fog-like glycerol molecules be condensed.

Although a particular embodiment of the invention has been described in detail for purposes of illustration, various modifications and enhancements may be made without departing from the spirit and scope of the invention. Accordingly, the invention is not to be limited except as by the appended claims.

What is claimed is:

1. A glycerol preparation method used with a glycerol preparation system comprising an industrial grade glycerol molecular distillatory unit for refining industrial grade glycerol of purity over 95%, said industrial grade glycerol molecular distillatory unit (500) comprising a pre-heater (501), a molecular still (502), a cold well (503), a semi-finished product accommodation tank (504), a semi-finished product output pump (505), a by-product accommodation tank (506), a by-product buffer tank (507), a by-product output pump (508), a vacuum buffer tank (509), an on-line gas-liquid separator (510), a vacuum pump (511), a thermal oil circulation pump (512), a thermal oil heater (513) and a thermal oil expansion tank (514), the glycerol preparation method comprising the steps of:

adding water to a water chiller (703) and then starting said water chiller (703) to make chilled water and to have the chilled water be pumped by an internal chilled water pump of said water chiller (703) to a condensing loop of said cold well (503) and a mechanical seal cooling loop of said molecular still (502) and then to a chilled water tank of said water chiller (703) to form a circulation loop;

after the chilled water reaching to a first temperature, starting said thermal oil circulation pump (512) to circulate a thermal oil from said thermal oil heater (513) through said expansion tank (514), said pre-heater (501) and said molecular still (502) and then to the thermal oil heater (513);

after the thermal oil reaching to a second temperature, starting said vacuum pump (511) to draw air from said molecular still (502), said semi-finished product accommodation tank (504) to lower the pressure of feeding and catching pipelines (517,518) of said industrial grade glycerol molecular distillatory unit (500);

operating a semi-finished product output pump (406) to pump a by-product of crude glycerol mixture out of a semi-finished product accommodation tank (404) of a crude glycerol mixture dehydrator unit (400) to said pre-heater (501), where the by-product of crude glycerol mixture is heated to a pre setting temperature, and then to the inside of a cylinder of said molecular still (502), where a wiper of the molecular still (502) is continuously rotated to apply the by-product of crude glycerol mixture to an inner cylindrical wall of the cylinder of the molecular still (502) so that the by-product of crude glycerol mixture forms a feedstock thin film; and continuously operating said thermal oil circulation pump (512) to circulate said thermal oil through a space between an inner cylindrical wall and outer casing of the cylinder of said molecular still (502) to keep the feedstock thin film at a pre setting temperature under the negative pressure of 40 Pa so that glycerol is evaporated from the feedstock thin film and the evaporated glycerol flows to an internal condenser of said molecular still (502) where the evaporated glycerol is condensed into an industrial glycerol and guided into said semi-finished product accommodation tank (504).

2. The glycerol preparation method as claimed in claim 1, wherein the first temperature is −10° C. and the second temperature is 240° C.; the glycerol preparation method further comprises the step of starting said vacuum pump (511) to draw air out of said industrial grade glycerol molecular distillatory unit (500) in lowering the pressure of the feeding and catching pipelines (517,518) of said industrial grade glycerol molecular distillatory unit (500) to below 40 Pa for enabling gas to be separated by said gas-liquid separator (510) and driven into the atmosphere by said vacuum pump (511) through an exhaust port of said vacuum pump (511).

3. The glycerol preparation method as claimed in claim 1, wherein the temperature of said pre-heater (501) is 240° C.; the feedstock thin film formed on the inner cylindrical wall of the cylinder of the molecular still (502) has a thickness about 4~5/1000 mm (4μ~5μ); 240° C. thermal oil is circulated through the space between the inner cylindrical wall and outer casing of the cylinder of said molecular still (502) to keep the feedstock thin film at a temperature above 195° C. so that the glycerol is evaporated from the feedstock thin film at 195° C. under the negative pressure 40 Pa.

4. The glycerol preparation method as claimed in claim 3, wherein the by-product left from the feedstock thin film after evaporation of the glycerol falls to a bottom side of said molecular still (502) and collected by a collector board (520) and then guided to said by-product buffer tank (507) and then pumped by said by-product output pump (508) when the level of the fluid mixture in said by-product buffer tank (507) reaches a pre setting level.

5. A glycerol preparation method used with a glycerol preparation system comprising a medical grade glycerol molecular distillatory unit for refining an industrial grade glycerol into a medical grade glycerol, said medical grade glycerol molecular distillatory unit (600) comprising a pre-heater (601), a molecular still-(602), a cold well (603), a by-product accommodation tank (604), a by-product output pump (605), a finished product accommodation tank (606), a finished product output pump (607), a vacuum buffer tank (608), an on-line gas-liquid separator (609), a vacuum pump (610), a thermal oil circulation pump (611), a thermal oil heater (612) and a thermal oil expansion tank (613), the glycerol preparation method comprising the steps of:

adding water to a water chiller (703) and then starting said water chiller (703) to make chilled water and to have the chilled water be pumped by an internal chilled water pump of said water chiller (703) to a condensing loop of said cold well (603) and a mechanical seal cooling loop of said molecular still (602) and then to a chilled water tank of said water chiller (703) to form a circulation loop;

after the chilled water reaching to a first temperature, starting said thermal oil circulation pump (611) to circulate a thermal oil from said thermal oil heater (612) through said expansion tank (613), said pre-heater (601) and said-molecular still (602) and then to the thermal oil heater (612);

after the thermal oil reaching to a second temperature, starting said vacuum pump (611) to draw air out of said molecular still (602) and said finished product accommodation tank (606) to lower the pressure of feeding and catching pipelines (617,618) of said medical grade glycerol molecular distillatory unit (600);

delivering an industrial glycerol from a semi-finished product accommodation tank (504) of an industrial grade glycerol molecular distillatory unit (500) to said pre-heater (601), where the industrial glycerol is heated to a pre setting temperature, and then to the inside of a cylinder of said molecular still (602), where a wiper of said molecular still (602) is continuously rotated to apply crude glycerol mixture to an inner cylindrical wall of the cylinder of said molecular still (602) so that the industrial grade glycerol forms an industrial grade glycerol thin film; and operating said thermal oil circulation pump (611) to circulate a thermal oil through a space between an inner cylindrical wall and outer casing of the cylinder of said molecular still (602) to have said industrial glycerol thin film be heated to above a pre setting temperature under the negative pressure of 40 Pa so that glycerol is evaporated from said industrial grade glycerol thin film and the evaporated glycerol flows to an internal condenser of said molecular still (602) where the evaporated glycerol is condensed into a medical glycerol and guided into said finished product accommodation tank (606).

6. The glycerol preparation method as claimed in claim 5, wherein the first temperature is −10° C. and the second temperature is 240° C.; the glycerol preparation method further comprises the step of starting said vacuum pump (611) to draw air out of said medical grade glycerol molecular distillatory unit (600) in lowering the pressure of the feeding and catching pipelines (617,618) of said medical grade glycerol molecular distillatory unit (600) to below 40 Pa for enabling gas to be separated by said gas-liquid separator (609) and driven into the atmosphere by said vacuum pump (611) through an exhaust port of said vacuum pump (611).

7. The glycerol preparation method as claimed in claim 5, wherein the temperature of said pre-heater (601) is 240° C.; the industrial glycerol thin film formed on the inner cylindrical wall of the cylinder of said molecular still (602) has a thickness about 4~5/1000mm (4μ~5μ); 240° C. thermal oil is circulated through the space between the inner cylindrical wall and outer casing of the cylinder of said molecular still (602) to have the industrial grade glycerol thin film be heated to above 195° C. so that an oil membrane of said industrial grade glycerol thin film starts to evaporate at 195° C. under the negative pressure 40 Pa.

8. The glycerol preparation method as claimed in claim 5, wherein the working pressure in the feeding and catching pipelines (617,618) is within the vacuum pressure 30~40 Pa so that the glycerol is evaporated from said industrial grade glycerol thin film at 195° C.

9. The glycerol preparation method as claimed in claim 5, wherein the by-product left from the industrial grade glycerol thin film after evaporation of the glycerol falls to a bottom side of said molecular still (602) and collected by a collector board (620) and then guided to said by-product buffer tank (604) and then pumped by said by-product output pump (605) when the level of the fluid mixture in said by-product buffer tank (604) reaches a pre setting level.

* * * * *